(12) United States Patent
Kamps et al.

(10) Patent No.: US 7,208,620 B1
(45) Date of Patent: Apr. 24, 2007

(54) POLYCYCLIC DIHYDROXY COMPOUNDS AND METHODS FOR PREPARATION

(75) Inventors: Jan Henk Kamps, Bergen op Zoom (NL); Jan-Pleun Lens, Breda (NL); A. S. Radhakrishna, Bangalore (IN); T. Tilak Raj, Bangalore (IN); Ravindra Vikram Singh, Basti (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/261,720

(22) Filed: Oct. 28, 2005

(51) Int. Cl.
*C07C 69/76* (2006.01)
*C07C 67/00* (2006.01)

(52) U.S. Cl. .......................... 560/76; 560/96
(58) Field of Classification Search ............... None
See application file for complete search history.

(56) References Cited

FOREIGN PATENT DOCUMENTS

JP         06-016800     *   1/1994

OTHER PUBLICATIONS

Rowland, et al. "Saponification of Dimethyl cis-2,6-Diphenyl-4-oxocyclohexane-1, 1-dicarboxylate. A Reinvestigation" J. Org. Chem. vol. 74, 1982, pp. 301-306.

Gomez-Bengoa, et al. "Michael Reaction of Stabilized Carbon Nucleophiles Catalyzed by [RuH2(PPh3)4]" J. Am. Chem. Soc. vol. 118, 1996, pp. 8553-8565.

Dewey, et al. "The Addition Reactions of Certain Pentadienones II. Addition of Malonic Esters" Pentadlenones and Malonic Esters, vol. 46, 1924, pp. 1267-1278.

* cited by examiner

*Primary Examiner*—Paul A. Zucker

(57) ABSTRACT

A dihydroxy aromatic compound having a Formula (I) wherein $R^1$ is selected from the group consisting of a cyano functionality, a nitro functionality, an aliphatic functionality having 1 to 10 carbons, an aliphatic ester functionality having 2 to 10 carbons, a cycloaliphatic ester functionality having 4 to 10 carbons and an aromatic ester functionality having 4 to 10 carbons; $R^2$ is selected from the group consisting of a cyano functionality, a nitro functionality, an aliphatic ester functionality having 2 to 10 carbons, a cycloaliphatic ester functionality having 4 to 10 carbons and an aromatic ester functionality having 4 to 10 carbons; and each $R^3$ and $R^4$, at each occurrence, can be the same or different and are independently at each occurrence an aliphatic functionality having 1 to 10 carbons or a cycloaliphatic functionality having 3 to 10 carbons, "n" is an integer having a value 0 to 4 and "m" is an integer having a value 0 to 4.

15 Claims, No Drawings

POLYCYCLIC DIHYDROXY COMPOUNDS AND METHODS FOR PREPARATION

BACKGROUND

This disclosure generally relates to polycyclic dihydroxy compounds. More particularly the disclosure relates to polycyclic dihydroxy aromatic compounds and methods for preparing the compounds.

Polycyclic dihydroxy compounds are generally known to be useful in the preparation of polycarbonates that exhibit exceptional properties like high glass transition temperature (Tg), high refractive index (RI), chemical resistance, and barrier properties. Materials having higher Tg and higher RI properties are in great demand for use in various applications like automotives and optical media.

Accordingly, there is a continuing need for new compounds that will provide polymers with better visual properties on account of high RI and at the same time retaining high Tg values, to enable their use at high temperatures to form a gamut of articles.

BRIEF SUMMARY

Disclosed herein are polycyclic dihydroxy compounds having Formula (I),

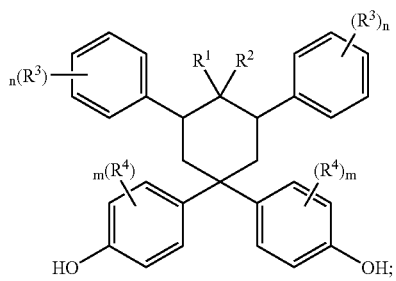

wherein $R^1$ is selected from the group consisting of a cyano functionality, a nitro functionality, an aliphatic functionality having 1 to 10 carbons, an aliphatic ester functionality having 2 to 10 carbons, a cycloaliphatic ester functionality having 4 to 10 carbons and an aromatic ester functionality having 4 to 10 carbons; $R^2$ is selected from the group consisting of a cyano functionality, a nitro functionality, an aliphatic ester functionality having 2 to 10 carbons, a cycloaliphatic ester functionality having 4 to 10 carbons and an aromatic ester functionality having 4 to 10 carbons; and each $R^3$ and $R^4$, at each occurrence, can be the same or different and are independently at each occurrence an aliphatic functionality having 1 to 10 carbons or a cycloaliphatic functionality having 3 to 10 carbons, "n" is an integer having a value 0 to 4 and "m" is an integer having a value 0 to 4.

In another embodiment a process for producing the polycyclic dihydroxy compounds of Formula (I) comprises reacting acetone with a compound of Formula (III) in the presence of a first catalyst to produce dibenzalacetone of Formula (IV)

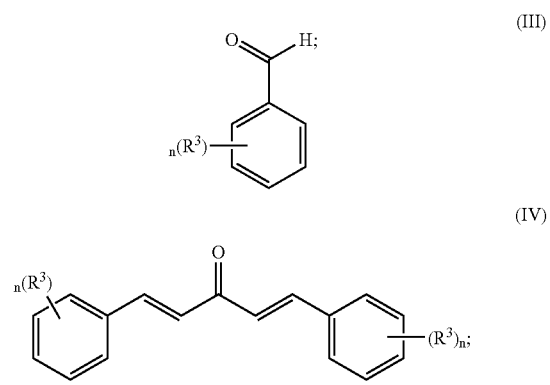

reacting the dibenzalacetone of Formula (IV) in the presence of a second catalyst with a compound of Formula (V) to produce a compound of Formula (VI)

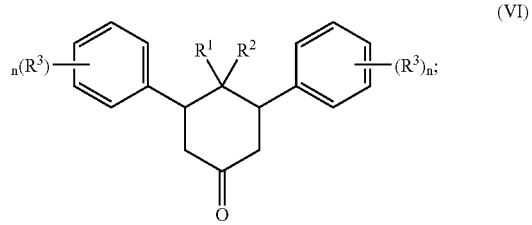

reacting the compound of Formula (VI) with a compound of Formula (VII) in the presence of an acid catalyst and a promoter to produce a compound of Formula (I),

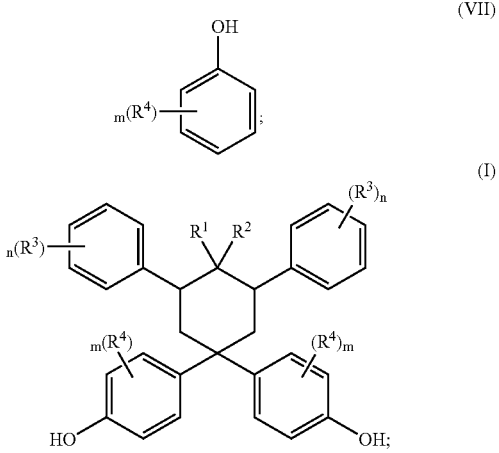

wherein $R^1$, $R^2$, $R^3$, $R^4$, "n" and "m" are defined as above.

In one embodiment a composition comprises a polycyclic dihydroxy compound having a Formula (I),

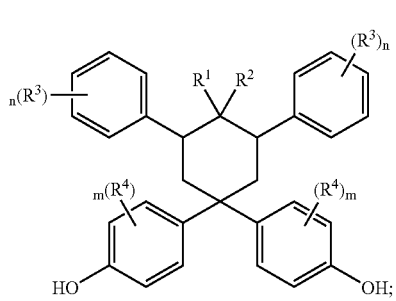

(I)

wherein R¹, R², R³, R⁴, "n" and "m" are defined as above.

In one embodiment a process for producing the polycyclic dihydroxy compounds of Formula (II) comprises reacting acetone with benzaldehyde having Formula (VIII) in presence of sodium hydroxide to produce dibenzalacetone having Formula (IX)

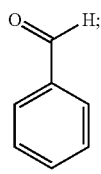

(VIII)

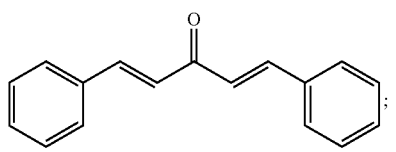

(IX)

reacting the dibenzalacetone having Formula (IX) in presence of sodium methoxide with dimethyl malonate having Formula (X) to produce methyl-2,6-diphenyl-cyclohexane-4-one-1,1-dicarboxylate having Formula (XI)

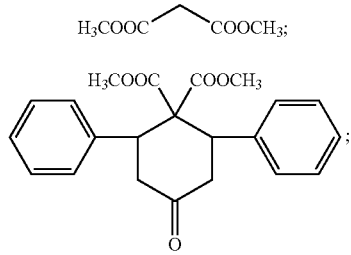

reacting methyl-2,6-diphenyl-cyclohexane-4-one-1,1-dicarboxylate with phenol having Formula (XII) in presence of an acid catalyst and a promoter to produce methyl-4,4'-bis(4-hydroxy-phenyl)-2,6-diphenyl-cyclohexane-1,1-dicarboxylate having Formula (II),

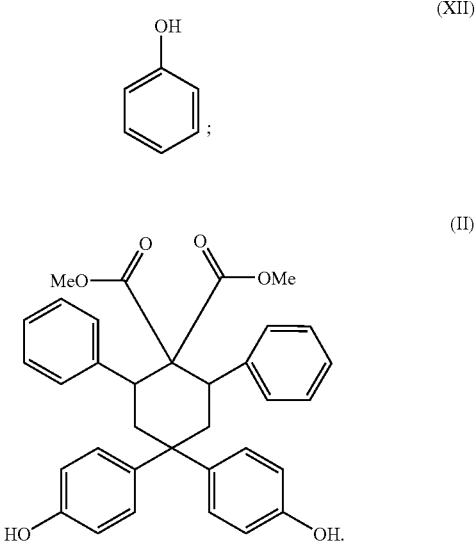

The disclosure may be understood more readily by reference to the following detailed description of the various features of the disclosure and the examples included therein.

DETAILED DESCRIPTION

Disclosed herein are polycyclic dihydroxy compounds and methods for preparing these compounds. These compounds may find applications as monomers in the preparation of polymers, especially in the preparation of polymers having high Tg and high RI.

The singular forms "a", "an" and "the" include plural referents unless the context clearly dictates otherwise. All ranges disclosed herein are inclusive and combinable (for example ranges of "up to 25 wt %, with 5 wt % to 20 wt % desired," is inclusive of the endpoints and all intermediate values of the ranges of "5 wt % to 25 wt %").

The modifier "about" used in connection with a quantity is inclusive of the stated value and has the meaning dictated by the context (for example, includes the degree of error associated with measurement of the particular quantity).

Cycloaliphatic ester functionality, as used herein, designates a cycloaliphatic functionality attached to a ester functionality, for example, cycloaliphatic-OC(O)—. Unless otherwise specified, the term "cycloaliphatic functionality" designates cyclic aliphatic functionalities having a valence of at least one, and comprising an array of atoms which is cyclic but which is not aromatic. A "cycloaliphatic functionality" may comprise one or more noncyclic components. For example, a cyclohexylmethyl group ($C_6H_{11}CH_2$—) is a cycloaliphatic functionality which comprises a cyclohexyl ring (the array of atoms which is cyclic but which is not aromatic) and a methylene group (the noncyclic component). The cycloaliphatic functionality may include heteroatoms such as nitrogen, sulfur, selenium, silicon and oxygen, or may be composed exclusively of carbon and hydrogen. For convenience, the term "cycloaliphatic functionality" is defined herein to encompass a wide range of functional groups such as alkyl groups, alkenyl groups, alkynyl groups, haloalkyl groups, conjugated dienyl groups, alcohol groups, ether groups, carboxylic acid groups, acyl groups (for example carboxylic acid derivatives such as esters and amides), amine groups and nitro groups. For example, the 4-methylcyclopent-1-yl group is a $C_6$ cycloaliphatic functionality comprising a methyl group, wherein the methyl group is a functional group which is an alkyl group. Similarly, the 2-nitrocyclobut-1-yl group is a $C_4$ cycloaliphatic functionality comprising a nitro group, wherein the nitro group is a functional group. A cycloaliphatic functionality may comprise one or more halogen atoms which may be the same or different. Halogen atoms include, for example, fluorine, chlorine, bromine, and iodine. Exemplary cycloaliphatic functionalities comprise cyclopropyl, cyclobutyl, 1,1,4,4-tetramethylcyclobutyl, piperidinyl, 2,2,6,6-tetramethylpiperydinyl and cyclohexyl, cyclopentyl.

As used herein, the term "aromatic ester functionality" refers to an array of atoms having a valence of at least one comprising at least one aromatic group attached to a ester functionality, for example, aromatic group-OC(O)—. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic functionality" includes but is not limited to phenyl, pyridyl, furanyl, thienyl, naphthyl, phenylene, and biphenyl functionalities. The aromatic functionality may also include nonaromatic components. For example, a benzyl group is an aromatic functionality that comprises a phenyl ring (the aromatic group) and a methylene group (the nonaromatic component). Similarly a tetrahydronaphthyl functionality is an aromatic functionality comprising an aromatic group ($C_6H_3$) fused to a nonaromatic component —$(CH_2)_4$—. For convenience, the term "aromatic functionality" is defined herein to encompass a wide range of functional groups such as alkyl groups, haloalkyl groups, haloaromatic groups, alcohol groups, ether groups, carboxylic acid groups, acyl groups (for example carboxylic acid derivatives such as esters and amides), amine groups and nitro groups. For example, the 4-methylphenyl functionality is a $C_7$ aromatic functionality comprising a methyl group, wherein the methyl group is a functional group which is an alkyl group. Similarly, the 2-nitrophenyl group is a $C_6$ aromatic functionality comprising a nitro group, wherein the nitro group is a functional group. Aromatic functionalities include halogenated aromatic functionalities. Exemplary aromatic functionalities include, but are not limited to phenyl, 4-trifluoromethylphenyl, 4-chloromethylphen-1-yl, 3-trichloromethylphen-1-yl (3-$CCl_3Ph$—), 4-(3-bromoprop-1-yl)phen-1-yl (4-$BrCH_2CH_2CH_2Ph$—), 4-aminophen-1-yl (4-$H_2NPh$—), 4-hydroxymethylphen-1-yl (4-$HOCH_2Ph$—), 4-methylthiophen-1-yl (4-$CH_3SPh$—), 3-methoxyphen-1-yl and 2-nitromethylphen-1-yl (2-$NO_2CH_2Ph$), naphthyl.

As used herein the term "aliphatic functionality" refers to an organic functionality having a valence of at least one consisting of a linear or branched array of atoms that is not cyclic. As used herein, the term "aliphatic ester functionality" refers to an array of atoms having a valence of at least one comprising at least one aliphatic functionality group attached to a ester functionality, i.e., aliphatic group-OC(O)—. Aliphatic functionalities are defined to comprise at least one carbon atom. The array of atoms comprising the aliphatic functionality may include heteroatoms such as nitrogen, sulfur, silicon, selenium and oxygen or may be composed exclusively of carbon and hydrogen. For convenience, the term "aliphatic functionality" is defined herein to encompass, as part of the "linear or branched array of atoms which is not cyclic" a wide range of functional groups such as alkyl groups, haloalkyl groups, alcohol groups, ether groups, carboxylic acid groups, acyl groups (for example carboxylic acid derivatives such as esters and amides), amine groups and nitro groups. For example, the 4-methylpent-1-yl is a $C_6$ aliphatic functionality comprising a methyl group, wherein the methyl group is a functional group which is an alkyl group. Similarly, the 4-nitrobut-1-yl group is a $C_4$ aliphatic functionality comprising a nitro group, wherein the nitro group is a functional group. An aliphatic functionality may be a haloalkyl group which comprises one or more halogen atoms which may be the same or different. Halogen atoms include, for example; fluorine, chlorine, bromine, and iodine. Exemplary aliphatic functionalities include, but are not limited to methyl, ethyl, propyl, isopropyl, butyl, isobutyl, pentyl, isopentyl, trifluoromethyl, bromodifluoromethyl, chlorodifluoromethyl, chloromethyl, trichloromethyl, bromoethyl, 2-hexyl, hexamethylene, hydroxymethyl (i.e., —$CH_2OH$), mercaptomethyl (—$CH_2SH$), methylthio (—$SCH_3$), methylthiomethyl (—$CH_2SCH_3$), methoxy, methoxycarbonyl ($CH_3OCO$—), nitromethyl (—$CH_2NO_2$) and thiocarbonyl.

Disclosed herein are polycyclic dihydroxy compounds having a Formula (I),

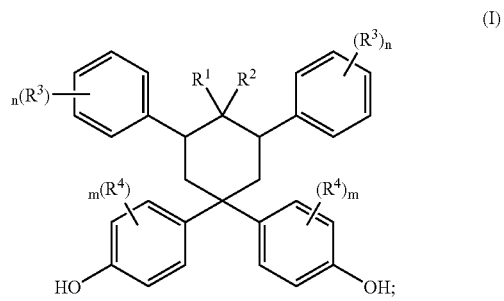

wherein $R^1$, $R^2$, $R^3$, $R^4$, "n" and "m" are defined as above.

In one embodiment the polycyclic dihydroxy compound comprises a compound of Formula (II)

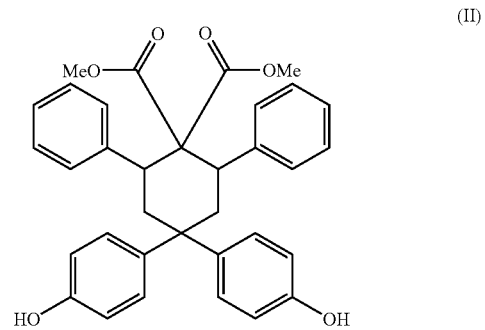

The compound of Formula (II) may hereinafter also be referred to as methyl-4,4-bis(4-hydroxyphenyl)-2,6-diphenyl cyclohexane-1,1-dicarboxylate.

The process for making the dihydroxy compound of Formula (I) comprises the following steps. The first step comprises reacting acetone with a compound of Formula (III) in the presence of a first catalyst to produce dibenzalacetone of Formula (IV)

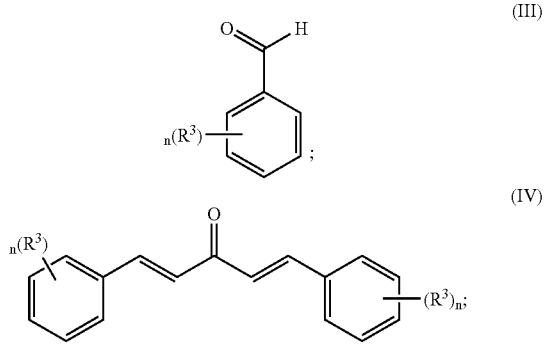

wherein R³ and "n" have the same meaning as defined above.

Exemplary compounds of Formula (III) include, but are not limited to benzaldehyde, 4-methyl benzaldehyde, 2-methyl benzaldehyde, 3-methyl benzaldehyde, 4-ethyl benzaldehyde, 2-ethyl benzaldehyde, 3-isopropyl-6-methyl benzaldehyde, 4-(N,N-dipropylamino)benzaldehyde, 4-ethoxybenzaldehyde, 4-butylbenzaldehyde, 4-tertbutyl benzaldehyde, and 4-isopropylbenzaldehyde. In one embodiment the compound of Formula (III) comprises benzaldehyde.

The amount of the compound of Formula (III) employed in the reaction can be about 2 to about 10 moles per mole of acetone employed. Within this range the amount may be greater than or equal to about 3 moles, or, more specifically, greater than or equal to about 6 moles. Also within this range the amount may be less than or equal to about 9 moles, or, more specifically less than or equal to about 7 moles.

Suitable first catalysts include but are not limited to alkali metal hydroxide and dry hydrogen chloride.

Specific examples of suitable alkali metal hydroxides that may be employed as the first catalyst in the reaction of acetone with the compound of Formula (III) include, but are not limited to sodium hydroxide, potassium hydroxide, lithium hydroxide, rubidium hydroxide cesium hydroxide or a combination of two or more of the foregoing alkali metal hydroxides. In one embodiment the alkali metal hydroxide comprises sodium hydroxide. The alkali metal hydroxides can be added as an aqueous solution or as solids. The amount of alkali metal hydroxide employed in the reaction can be about 6 moles to about 15 moles per mole of acetone employed. Within this range the amount may be greater than or equal to about 7 moles, or, more specifically greater than or equal to about 9 moles. Also within this range the amount may be less than or equal to about 13 moles, or, more specifically less than or equal to about 12 moles.

Specific examples of suitable solvents that can be employed in the reaction of acetone with a compound of Formula (III) in the presence of an alkali earth metal hydroxide to produce the dibenzalacetone of Formula (IV) include, but are not limited know ethanol, methanol, isopropanol, n-propanol, n-butanol, isobutanol or mixtures of two or more of the foregoing solvents. In one embodiment the solvent employed comprises ethanol, methanol, or a combination of ethanol and methanol. The amount of solvent employed in the reaction of acetone with a compound of Formula (III) in the presence of an alkali earth metal hydroxide to produce the dibenzalacetone of Formula (IV) can be about 2 liters to about 10 liters per mole of acetone. Within this range the amount may be greater than or equal to about 3 liters, or, more specifically, greater than or equal to about 5 liters. Also within this range the amount may be less than or equal to about 9 liters, or, more specifically less than or equal to about 7 liters.

The temperature at which the reaction of acetone with the compound of Formula (III) occurs to produce the dibenzalacetone of Formula (IV) is about 20° C. to about 40° C. Within this range the temperature may be greater than or equal to about 22° C., or, more specifically, greater than or equal to about 25° C. Also within this range the temperature may be less than or equal to about 35° C., or, more specifically, less than or equal to about 30° C. The time taken for the reaction of acetone with the compound of Formula (III) to produce the dibenzalacetone of Formula (IV) can be about 15 minutes to about 4 hours. Within this range the time may be greater than or equal to about 1 hour, or, more specifically, greater than or equal to about 1.5 hours. Also within this range the time may be less than or equal to about 3 hours, or, more specifically, less than or equal to about 2 hours.

The second step comprises reacting the dibenzalacetone of Formula (IV) in the presence of a second catalyst with a compound of Formula (V) to produce a compound of Formula (VI)

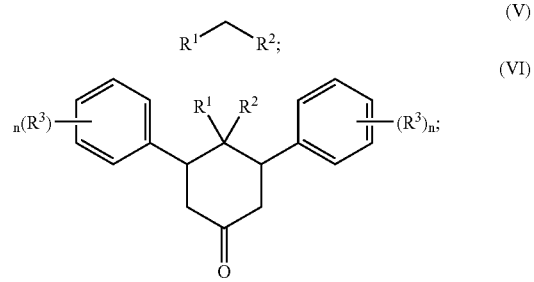

wherein R¹, R², R³, and "n" have the same meaning as defined above.

Suitable compounds having Formula (V) include, but are not limited to dimethyl malonate, diethyl malonate, diisopropyl malonate, ethyl cyanoacetate and methyl cyanoacetate. In one embodiment the compound of Formula (V) may comprise dimethyl malonate or ethyl cyanoacetate.

The amount of the compound of Formula (V) employed in the reaction can be about 1 mole to about 6 moles per mole of dibenzalacetone compound having Formula (IV). Within this range the amount may be greater than or equal to about 2 moles, or, more specifically, greater than or equal to about 2.5 moles. Also within this range the amount may be less than or equal to about 5.5 moles, or, more specifically, less than or equal to about 5 moles.

Suitable second catalysts include, but are not limited to an alkoxide, glacial acetic acid with sulfuric acid, ammonium ylides, 1,4-diazabicyclo[2.2.2] octane, rhodium acetate, sodium carbonate or benzyltriethylammonium hydroxide (hereinafter also mentioned as Triton® B).

Specific examples of alkoxides that may be employed as second catalysts in the reaction of compound having Formula (IV) with the compound of Formula (V) include, but are not limited to aluminum isopropoxide, aluminum phenoxide, aluminum tributoxide, lithium 2-ethylhexodide, lithium ethoxide, lithium isopropoxide, lithium methoxide, magnesium ethoxide, magnesium methoxide, potassium ethoxide, potassium isobutoxide, potassium methoxide, potassium tert-butoxide, sodium benzyloxide, sodium ethoxide, sodium phenoxide, sodium tert-butoxide, sodium tert-pentoxide, sodium methanethiolate, or mixtures of two or more of the foregoing. In one embodiment the alkoxide employed is sodium methoxide.

Specific examples of suitable solvents that may be employed in the reaction of compound having Formula (IV) in the presence of alkoxide, with the compound of Formula (V) include, but are not limited to ethanol, methanol, isopropanol, n-propanol, n-butanol, isobutanol or mixtures of two or more of the foregoing. In one embodiment the solvent employed comprises ethanol, methanol, or a combination of methanol and ethanol. The amount of solvent employed in the reaction of compound having Formula (IV) in the presence of alkoxide with the compound of Formula (V) comprises about 1 liter to about 10 liters per mole of dibenzalacetone compound having Formula (IV). Within this range the amount may be greater than or equal to about 2 liters, or, more specifically, greater than or equal to about 3 liters. Also within this range the amount may be less than or equal to about 6 liters, or, more specifically, less than or equal to about 5 liters.

The temperature of the reaction of compound having Formula (IV) in the presence of alkoxide, with the compound of Formula (V) can be about 50° C. to about 80° C. Within this range the temperature may be greater than or equal to about 55° C., or, more specifically, greater than or equal to about 60° C. Also within this range the temperature may be less than or equal to about 75° C., or, more specifically, less than or equal to about 70° C. The time for the reaction of compound having Formula (IV) in the presence of alkoxide, with the compound of Formula (V) can be about 3 hours to about 24 hours. Within this range the time may be greater than or equal to about 4, or, more specifically, greater than or equal to about 6. Also within this range the time may be less than or equal to about 16 hours, or, more specifically, less than or equal to about 12 hours.

The amount of alkoxide employed in the reaction can be about 0.01 to about 0.6 mole per mole of dibenzalacetone compound of Formula (IV). Within this range the amount may be greater than or equal to about 0.02 moles, or, more specifically, greater than or equal to about 0.08 moles. Also within this range the amount may be less than or equal to about 0.5 moles, or, more specifically, less than or equal to about 0.4 moles.

The third step comprises reacting the compound of Formula (VI) with a compound of Formula (VII) in the presence of an acid catalyst and a promoter to produce the compound of Formula (I),

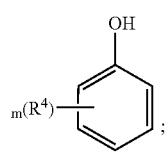
(VII)

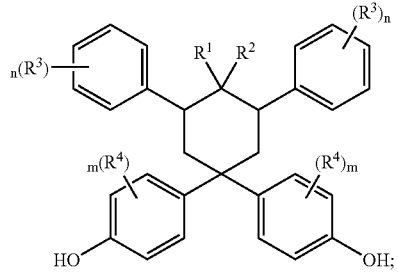
(I)

wherein $R^1$, $R^2$, $R^3$, $R^4$, "n" and "m" have the same meaning as defined above.

Specific examples of suitable compounds of Formula (VII) include, but are not limited to phenol, 2,6-dimethylphenol, 2,3,6-trimethylphenol, 2,6-di-tert-butylphenol, 2-tert-butylphenol, meta-cresol, ortho-cresol, ortho-phenylphenol, ortho-chlorophenol, ortho-benzylphenol, ortho-vinylphenol, and mixtures of two or more of the foregoing. In one embodiment, the compound of Formula (VII) comprises phenol, m-cresol, o-cresol, or a mixture of two or more of the foregoing. In another embodiment the compound of Formula (VII) is phenol.

The amount of the compound of Formula (VII) employed in the reaction can be about 5 moles to about 20 moles per mole of compound of Formula (VI). Within this range the amount may be greater than or equal to about 6 moles, or, more specifically, greater than or equal to about 8 moles. Also within this range the amount may be less than or equal to about 15 moles, or, more specifically, less than or equal to about 10 moles.

Suitable acid catalysts that may be employed in the reaction of the compound having Formula (VI) with the compound of Formula (VII) include, but are not limited to mineral acids, cation exchange resins and solid acid catalysts. Non-limiting examples of mineral acids include hydrogen chloride liquid, hydrogen chloride gas, sulfuric acid and nitric acid. As used herein the term "cation exchange resin" refers to an ion exchange resin in the hydrogen form, wherein the hydrogen ions are bound to the active sites which can be removed either by dissociation in solution or by replacement with other positive ions. The active sites of the resin have different attractive strengths for different ions, and this selective attraction serves as a means for ion exchange. Non-limiting examples of suitable cation exchange resins include the series of sulfonated divinylbenzene-crosslinked styrene copolymers, such as for example, copolymers crosslinked with about 1 to about 20 weight percent of divinylbenzene relative to the overall weight of the acidic ion exchange resin. More specifically, suitable catalysts include cation exchange resins crosslinked with greater than or equal to about 8 weight percent of divinylbenzene relative to the overall weight of the acidic ion exchange resin catalyst, such as for example, Amberlyst 15® commercially available from Aldrich Chemical Company, Bayer K2431® commercially available from Bayer Company and T-66® commercially available from Thermax, Ltd.

In one embodiment the amount of acid catalyst employed in the reaction can be about 0.5 weight percent to about 10 weight percent of an overall weight of the reaction mixture. Within this range the amount may be greater than or equal to about 1 weight percent, or, more specifically, greater than or equal to about 3 weight percent. Also within this range the amount may be less than or equal to about 8 weight percent, or, more specifically, less than or equal to about 5 weight percent. As used herein, the term "reaction mixture" refers to a mixture comprising the compounds of Formula (VI) and Formula (VII). As used herein, the term "overall weight of the reaction mixture" refers to the weight of a reaction mixture comprising the compounds of Formula (VI) and Formula (VII).

Suitable examples of promoters include, but are not limited to 3-mercaptopropionic acid (hereinafter called 3-MPA), a substituted or an unsubstituted benzyl mercaptan, 3-mercapto-1-propanol, ethyl 3-mercaptopropionate, 1,4-bis (mercaptomethyl)benzene, 2-mercaptoethane-sulfonic acid, 3-mercaptopropanesulfonic acid, 4-mercaptobutanesulfonic acid, 4-mercaptopentane-sulfonic acid, 3-mercapto-2,2-dimethylpropanesulfonic acid, 2,3-dimercaptopropane-sulfonic acid, mercaptopropane-2,3-disulfonic acid, 2-benzyl-4-mercaptobutanesulfonic acid, 5-mercaptopentane-sulfonic acid, methanethiol, ethanethiol, isopropanethiol, butanethiol, resorcinol, catechol, hytdroquionone, or the mono- and di-methyl or mono- and di-ethyl ethers thereof, para-ethylphenol, ortho-cresol, para-cresol, phloroglucinol, alpha-naphthol, 5-methyl-alpha-naphthol, 6-isobutyl-alpha-naphthol, 1,4-dihydroxynaphthalene, 6-hexyl-1,4-dihydroxy naphthalene and 6-methyl-4-methoxy-alpha-naphthalene. In one embodiment resorcinol or 3-mercaptopropionic acid is employed as the promoter.

In one embodiment the amount of promoter employed in the reaction is about 0.2 moles to about 0.5 moles based on the moles of the compound of Formula (VI) employed. Within this range the amount may be greater than or equal to about 0.25 moles, or, more specifically greater than or equal to about 0.3 moles. Also within this range the amount may be less than or equal to about 0.45 moles, or, more specifically, less than or equal to about 0.4 moles.

Specific examples of suitable solvents that may be employed in the reaction of compound having in the reaction of the compound having Formula (VI) with the compound of Formula (VII) include, but are not limited to toluene, petroleum ether, xylene, benzene hexane, heptane, octane, decane or a mixture of two or more of the foregoing solvents. In one embodiment the solvent employed comprises toluene or petroleum ether. In another embodiment the solvent employed comprises toluene. The amount of solvent employed in the reaction of the compound having Formula (VI) with the compound of Formula (VII) can be about 1 liter to about 10 liters per mole of Formula (VI) employed. Within this range the amount may be greater than or equal to about 2 liters, or, more specifically, greater than or equal to about 3 liters. Also within this range the amount may be less than or equal to about 6 liters, or, more specifically, less than or equal to about 5 liters. In one embodiment an excess of the compound of Formula (VII) may be employed as the solvent in the reaction.

The temperature at which the reaction of the compound having Formula (VI) with the compound of Formula (VII) can be about 40° C. to about 120° C. Within this range the temperature may be greater than or equal to about 45° C., or, more specifically, greater than or equal to about 60° C. Also within this range the temperature may be less than or equal to about 100° C., or, more specifically, less than or equal to about 80° C. The time taken for the reaction of the compound having Formula (VI) with the compound of Formula (VII) can be about 10 hours to about 16 hours. Within this range the time may be greater than or equal to about 12 hours, or, more specifically, greater than or equal to about 13 hours. Also within this range the time may be less than or equal to about 15 hours, or, more specifically, less than or equal to about 14 hours.

The product compound having Formula (I) may be isolated by using appropriate methods. For example when isolating compounds having Formula (I) the reaction mixture may be initially mixed with an organic solvent or a mixture of organic solvents such as toluene and petroleum ether and filtered. The resultant filter cake may be suspended in hot water and filtered again. In some cases the resulting solids may further be crystallized from a solvent such as isopropanol.

In one embodiment a composition comprises a compound of Formula (I)

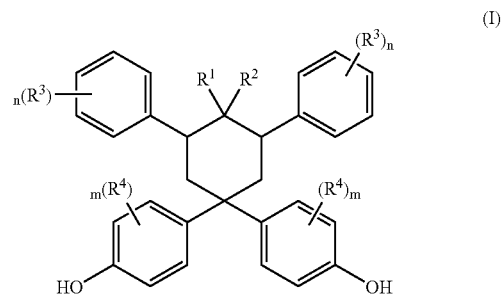

wherein $R^1$, $R^2$, $R^3$, $R^4$, "n" and "m" have the same meaning as defined above.

As previously discussed, one of the end uses of the compounds of Formula (I) is use in the preparation of polymers for example, polycarbonates, polyesters, polyurethanes, and epoxides. Suitable methods for preparation of polycarbonates include, but are not limited to interfacial polymerization where compounds of Formula (I) react with phosgene, and melt-transesterification reactions of the compound of Formula (I) and possibly other bisphenols with e.g. diphenylcarbonate in the presence of quaternary phosphonium salts, tetraalkylammonium salts, and/or sodium hydroxide as catalyst systems.

A further understanding of the techniques described above can be obtained by reference to certain specific examples that are provided herein for purposes of illustration only, and are not intended to be limiting.

EXAMPLES

Proton NMR spectra for all the starting materials and products described herein were measured using a 300 megahertz Bruker NMR spectrometer using deuterated chloroform or $Cd_6$-dimethylsulfoxide as a solvent. Compounds were further characterized by a liquid chromatograph-mass spectrometer (LC-MS) system, comprising a liquid chromatograph and a Quattro Ultima Pt mass spectrometer.

Liquid Chromatographic (LC) method was used to identity the conversion of product compound. A Xterra C18 column, length 50 meters, inner diameter 4.6 millimeters and thickness 5 micrometers was used for the analysis. The column temperature was maintained at 30° C. The column was eluted with a ratio of water to acetonitrile of 80:20. The flow rate of sample in the column was maintained at 1.00 milliliter per minute (ml/min) and the amount of sample injected was 5 micro liter. The total run time was 23 min.

Example 1

This example provides a method for the preparation of methyl-4,4'-bis(4-hydroxy-phenyl)-2,6-diphenyl-cyclohexane-1,1-dicarboxylate (Formula (I)). The method includes 3 steps as described below.

STEP A: Preparation of Dibenzalacetone (Formula (IV))

To an aqueous solution of sodium hydroxide (200 grams (g) in one liter of water) was added ethanol (1.6 liters; purity greater than 95%) and the resultant mixture was stirred well. Another mixture having acetone (29 g) and benzaldehyde (106 g) was added to this solution under stirring. A yellow colored precipitate was observed. The stirring was continued for about 15 minutes (min). Subsequently additional acetone (29 g) and benzaldehyde (106 g) were added and the mixture was stirred for another 45 min. The yellow colored precipitate was separated by filtration, washed with water (2 liters), and dried at room temperature to get 223 g of crude dibenzalacetone. Melting point of the compound was obtained as 104–106° C. This product was used in the next step without further purification.

STEP B: Preparation of methyl-2,6-diphenyl-cyclohexane-4-one-1,1-dicarboxylate (Formula (VI)). Dimethyl malonate (58 g) was added to a clear solution of dibenzalacetone (93.6 g, as prepared in STEP A) in absolute methanol (1.2 liters) and the resultant reaction mixture was stirred well. To this reaction mixture was added 5% sodium methoxide solution (20 ml) under stirring. The color of the reaction mixture is observed to change from yellow to orange color almost immediately. The stirring was then continued for another 4–6 hours at 60° C. The reaction mixture was then allowed to cool to room temperature, and left overnight. The colorless white precipitate was separated by filtration and washed with chilled methanol to get about 111 g of product. The filtrate was concentrated to 30% of its volume to recover the second crop of 12 g. Melting point of the combined product (first crop+second crop) was observed as 135° C. This material was used in the next step without purification.

STEP C: Preparation of methyl-4,4'-bis(4-hydroxy-phenyl)2,6-diphenyl-cyclohexane-1,1-dicarboxylate (Formula (I)).

A mixture of methyl-2,6-diphenyl-cyclohexane-4-one-1,1-dicarboxylate (109.8 g; prepared in STEP B), phenol (141 g) and resorcinol (6.27 g), was heated to 60° C. in a three necked reaction flask to obtain a homogenous solution. Dry hydrogen chloride gas was purged into the reaction mixture for 12 hours and the temperature was maintained at 60° C. After 12 hours, the reaction mixture was allowed to attain room temperature over a period of 2 to 3 hours. At the end of this time, white precipitate was observed in the reaction flask. Toluene (200 ml) was added to the reaction mixture and stirred for about 30 minutes and the resultant mixture was filtered. The filter cake obtained was triturated with 1.5 liters of 1:1 mixture of toluene and petroleum ether and stirred for about 15 minutes. The solid was filtered and dried to get a yellow cake which was further suspended in hot water (500 ml), stirred for about 5 minutes and filtered again. The obtained solid was crystallized with isopropanol to get a crystalline white methyl-4,4'-bis(4-hydroxy-phenyl)-2,6-diphenyl-cyclohexane-1,1-dicarboxylate with a yield of about 101 g and having a melting point greater than 270° C. The solid was dissolved in deuterated chloroform and analyzed using NMR. The corresponding peaks obtained were at δ 2.35–2.73 (4H, m, $CH_2$), 3.0–3.2(6H, s, $OCH_3$), 3.25–3.75(2H, br-s, OH), 4.26–4.52(2H, m, CH), 6.68–6.81 (4H, dd, Ar—H), 6.97–7.07(4H, dd, Ar—H), 7.16–7.4(10H, m, Ar—H).

Example 2

Preparation of methyl-1-cyano-4,4'-bis(4-hydroxy-phenyl) 2,6-diphenyl-cyclohexane-1-carboxylate (Formula (I)).

STEP I: Cyanoethyl acetate (13.3 g) and Triton®-B (Benzyltriethylammonium hydroxide); 20–22 drops) were added to a suspension of dibenzalacetone (25.0 g; as prepared in step A of example I above) in absolute ethanol (200 cc) and the resultant mixture was stirred well. A clear solution was obtained which immediately changed to a thick white precipitate. Ethanol (150 cc) was added to the reaction mass and stirred well for about 1–2 hours at 0° C. The colorless precipitate obtained was separated by filtration, washed with chilled ethanol to obtain 22.3 g of methyl-1-cyano-2,6-diphenyl-cyclohexane-4-one-1, 1-carboxylate having a melting point of about 133–138° C. This material was used in step II without purification. The solid was analyzed using NMR (Acetone-$D_6$). The corresponding peaks were at δ 0.70–0.78 (3H, t), 2.65–3.05(4H, m), 3.45–4.17(4H, m), 7.32–7.45(10H, br-s).

Step II: A mixture of methyl-1-cyano-2,6-diphenyl-cyclohexane-4-one-1,1-carboxylate (34.8 g; as prepared in step I), phenol (47 g) and resorcinol (2.05 g), was heated to 60° C. in a three necked reaction flask until a homogenous solution was obtained. Dry hydrogen chloride gas was passed into the reaction mixture for 12 hours maintaining the temperature at 60° C. After 12 hours, the reaction mixture was allowed to attain room temperature and during this period formation of white precipitate was observed. Toluene (100 ml) was added to the reaction mixture and the reaction mixture stirred for 30 minutes. The resultant solid was filtered. The solid cake was triturated with 500 ml of 1:1 mixture of toluene and petroleum ether and the resultant mixture stirred for about 15 minutes. The mixture was filtered. The filter cake on drying provided a yellow cake which was further suspended in hot water (500 ml, temperature 70° C.), stirred for about 15 minutes and filtered again. The resultant solid was crystallized with isopropanol to get a crystalline white solid weighing 36.3 g, having a melting point greater than 250° C. The solid was dissolved in deuterated acetone and analyzed using NMR. The corresponding peaks were at δ 0.70–0.78 (3H, t), 2.65–3.05(4H, m), 3.45–4.17(4H, m), 6.74–6.85(4H, dd), 7.05–7.15(4H, dd), 7.32–7.45(10H, br-s), 8.23 (2H.br-s).

As can be seen from the foregoing examples a compound having Formula (I) can be readily prepared as shown in Examples 1 and 2.

While the invention has been described with reference to an exemplary embodiment, it will be understood by those skilled in the art that various changes may be made and equivalents may be substituted for elements thereof without departing from the scope of the invention. In addition, many modifications may be made to adapt a situation or material to the teachings of the invention without departing from the essential scope thereof. Therefore, it is intended that the invention not be limited to the embodiment disclosed as the best mode contemplated for carrying out this invention, but that the invention will include all embodiments falling within the scope of the appended claims.

The invention claimed is:

1. A dihydroxy aromatic compound having a Formula (I),

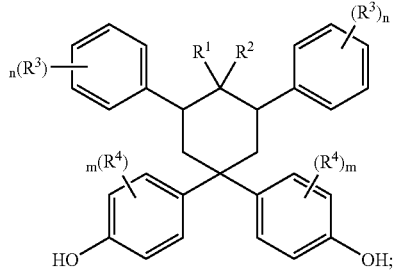

wherein $R^1$ is selected from the group consisting of a cyano functionality, a nitro functionality, an aliphatic functionality having 1 to 10 carbons, an aliphatic ester functionality having 2 to 10 carbons, a cycloaliphatic ester functionality having 4 to 10 carbons and an aromatic ester functionality having 4 to 10 carbons; $R^2$ is selected from the group consisting of a cyano functionality, a nitro functionality, an aliphatic ester functionality having 2 to 10 carbons, a cycloaliphatic ester functionality having 4 to 10 carbons and an aromatic ester functionality having 4 to 10 carbons; and each $R^3$ and $R^4$, at each occurrence, can be the same or different and are independently at each occurrence an aliphatic functionality having 1 to 10 carbons or a cycloaliphatic functionality having 3 to 10 carbons; "n" is an integer having a value 0 to 4 and "m" is an integer having a value 0 to 4.

2. The dihydroxy aromatic compound of claim 1 having a Formula (II)

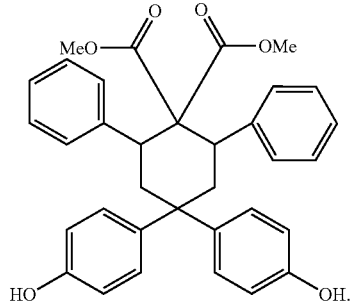

3. A process comprising;
reacting acetone with a compound of Formula (III) in the presence of a first catalyst to produce dibenzalacetone of Formula (IV)

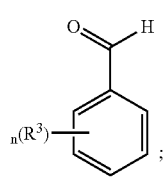

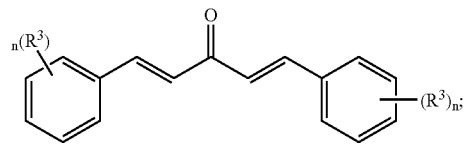

reacting the dibenzalacetone of Formula (IV) in the presence of a second catalyst with a compound of Formula (V) to produce a compound of Formula (VI)

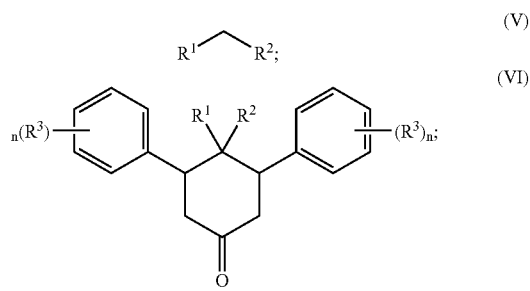

reacting the compound of Formula (VI) with a compound of Formula (VII) in the presence of an acid catalyst and a promoter to produce a compound of Formula (I),

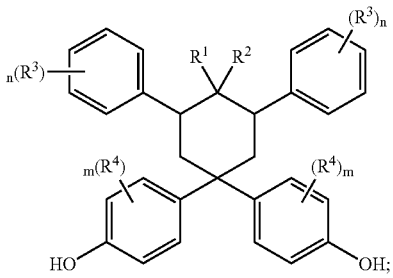

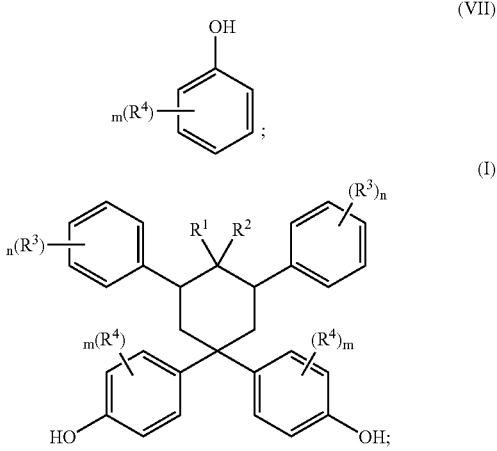

wherein $R^1$ is selected from the group consisting of a cyano functionality, a nitro functionality, an aliphatic functionality having 1 to 10 carbons, an aliphatic ester functionality having 2 to 10 carbons, a cycloaliphatic ester functionality having 4 to 10 carbons and an aromatic ester functionality having 4 to 10 carbons; $R^2$ is selected from the group consisting of a cyano functionality, a nitro functionality, an aliphatic ester functionality having 2 to 10 carbons, a cycloaliphatic ester functionality having 4 to 10 carbons and an aromatic ester functionality having 4 to 10 carbons; and each $R^3$ and $R^4$, at each occurrence, can be the same or different and are independently at each occurrence an aliphatic functionality having 1 to 10 carbons or a cycloaliphatic functionality having 3 to 10 carbons; "n" is an integer having a value 0 to 4 and "m" is an integer having a value 0 to 4.

4. The process of claim 3 wherein the compound of Formula (III) comprises benzaldehyde.

5. The process of claim 3 wherein the compound of Formula (V) comprises dimethyl malonate.

6. The process of claim 3 wherein the compound of Formula (VII) comprises phenol.

7. The process of claim 3 wherein the promoter comprises resorcinol or 3-mercaptopropionic acid.

8. The process of claim 3 wherein the acid catalyst comprises hydrogen chloride gas.

9. The process of claim 3 wherein the first catalyst comprises alkali metal hydroxide, dry hydrogen chloride or glacial acetic acid with sulfuric acid.

10. The process of claim 9 wherein the first catalyst comprises sodium hydroxide.

11. The process of claim 3 wherein the second catalyst comprises alkoxide, ammonium ylides, 1,4-diazabicyclo [2.2.2] octane, rhodium acetate, sodium carbonate or benzyltriethylammonium hydroxide.

12. The process of claim 3, wherein the reaction of acetone with a compound of Formula (III) occurs at a temperature of about 20° C. to about 40° C.

13. The process of claim 3, wherein the reaction of the dibenzalacetone of Formula (IV) with the compound of Formula (V) occurs at a temperature of about 40° C. to about 80° C.

14. The process of claim 3, wherein the reaction of the compound of Formula (VI) with the compound of Formula (VII) occurs at a temperature of about 40° C. to about 80° C.

15. A process comprising;
reacting acetone with benzaldehyde having Formula (VIII) in presence of sodium hydroxide to produce dibenzalacetone having Formula (IX)

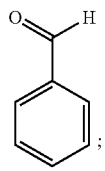

(VIII)

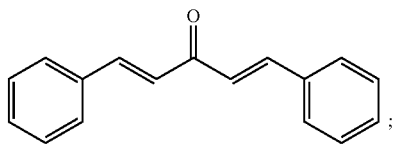

(IX)

reacting the dibenzalacetone having Formula (IX) in presence of sodium methoxide with dimethyl malonate having Formula (X) to produce methyl-2,6-diphenyl-cyclohexane-4-one-1,1-dicarboxylate having Formula (XI)

(X)

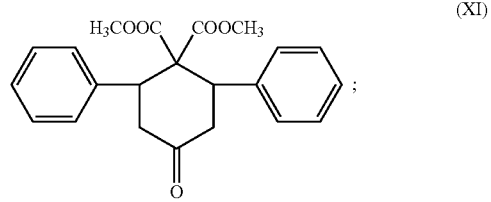

(XI)

reacting methyl-2,6-diphenyl-cyclohexane-4-one-1,1-dicarboxylate with phenol having Formula (XII) in presence of an acid catalyst and a promoter to produce methyl-4,4'-bis(4-hydroxy-phenyl)-2,6-diphenyl-cyclohexane-1,1-dicarboxylate having Formula (II),

(XII)

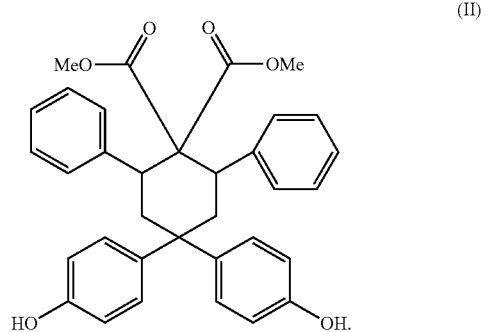

(II)

* * * * *